United States Patent [19]
Palfreyman et al.

[11] Patent Number: 4,916,140
[45] Date of Patent: Apr. 10, 1990

[54] ANTIEPILEPTIC PYRAZOLOPYRIDINES
[75] Inventors: Michael G. Palfreyman, Cincinnati; Francis P. Miller, Loveland, both of Ohio; Anis Mir, Bartenheim, France
[73] Assignee: Merrell Dow Pharmaceuticals Inc., Cincinnati, Ohio
[21] Appl. No.: 250,478
[22] Filed: Sep. 28, 1988
[51] Int. Cl.$^4$ .............................................. A61K 31/44
[52] U.S. Cl. ....................................................... 514/299
[58] Field of Search ................................. 514/300, 299
[56] References Cited
PUBLICATIONS Little et al., *Life Sciences*, vol. 39, pp. 2059-2065 (1986).
Wauquier et al., *Drug Development Research*, 7:49-60 (1986).
M. J. Brodie, *British Medical Journal*, vol. 296, pp. 530-531 (1988).
C. D. Binnie, "Clinical Trials of Flunarizine in Epilepsy", Intl. Symposium on Calcium Antagonists, New York City, Feb. 10-13, 1987.
F. B. Meyer et al., "Anticonvulsant Properties of Dihydropyridine Ca$^{2+}$ Antagonists" Intl. Symposium on Calcium Antagonists, New York City, Feb. 10-13, 1987.
A. Scriabine, "Pharmacology of Nimodipine—A Review", Intl. Symposium on Calcium Antagonists, New York City, Feb. 10-13, 1987.
M. R. Tata et al., "Flunarizine in Pharmacoresistant Epilepsies: Preliminary Experiences in 30 Cases", Intl. Symposium on Calcium Antagonists, New York City, Feb. 10-13, 1987.
D. M. Treiman, "Calcium Antagonists in the Treatment of Epilepsy", Intl. Symposium on Calcium Antagonists, New York City, Feb. 10-13, 1987.
R. Trouve et al., "Nitrendipine: An Antidote to the Lethal Toxicity of Cocaine", Intl. Symposium on Calcium Antagonists, New York City, Feb. 10-13, 1987.

*Primary Examiner*—Stanley J. Friedman
*Attorney, Agent, or Firm*—Michael J. Sayles

[57] ABSTRACT

The disclosure pertains to certain pyrazolopyridincarboxylates which are calcium channel blockers and possess anticonvulsant properties. By virtue of this activity, the compounds are useful in the treatment of epilepsy.

5 Claims, No Drawings

ANTIEPILEPTIC PYRAZOLOPYRIDINES

FIELD OF THE INVENTION

This invention relates to the use of certain pyrazolopyridine calcium channel blockers in the treatment of epilepsy by virtue of their anticonvulsant activity.

BACKGROUND OF THE INVENTION

Evidence suggests that blockers of calcium channels may have anticonvulsant activity. While this may be true, few calcium channel blockers pass the blood brain barrier. Anticonvulsant activity has been demonstrated for nifedipine, but its use as an antiepileptic has not been fully demonstrated. Applicants have now discovered a class of calcium channel blockers which are effective as anticonvulsants and would therefore be useful in the treatment of epilepsy.

SUMMARY OF THE INVENTION

The present invention is directed to the antiepileptic use of a class of pharmacologically active 4,7-dihydropyrazolo[3,4-b]pyridines of formula

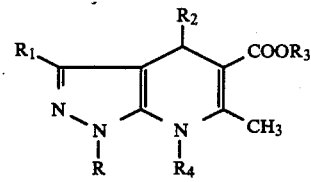

wherein

R represents hydrogen, $(C_1-C_6)$alkyl, $(C_1-C_6)$alkenyl, $(C_3-C_7)$cycloalkyl, phenyl which is optionally substituted by 1, 2 or 3 substituents selected from $(C_1-C_4)$alkyl, $(C_1-C_4)$alkoxy, chloro, fluoro, bromo, nitro, and $(C_1-C_6)$alkoxycarbonyl, or phenyl $(C_1-C_4)$alkyl, wherein the phenyl group is optionally substituted as above;

$R_1$ represents hydrogen, $(C_1-C_6)$alkyl, $(C_2-C_6)$alkenyl, $(C_3-C_7)$cycloalkyl, $(C_1-C_6)$alkoxycarbonyl, phenyl optionally substituted as above, or phenyl $(C_1-C_4)$alkyl, optionally substituted as above;

$R_2$ represents phenyl groups optionally substituted with 1, 2 or 3 substituents selected from $(C_1-C_4)$alkyl, $(C_1-C_4)$alkoxy, halo$(C_1-C_4)$alkyl, chloro, bromo, fluoro, nitro, cyano, $(C_1-C_6)$alkoxycarbonyl, and a group of formula $S(O)n$-$(C_1-C_6)$alkyl, wherein n represents zero or the integer 1 or 2, or $R_2$ represents a pentafluorophenyl group, an α- or β-naphthyl group, an aromatic 5-6 membered heterocycle ring such as furanyl or thienyl, a group of formula

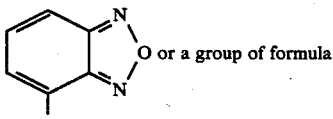 or a group of formula

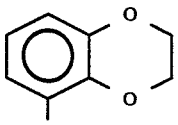

wherein $R_3$ represents $(C_1-C_6)$alkyl, $(C_2-C_6)$alkenyl, phenyl optionally substituted as above, and phenyl$(C_1-C_4)$alkyl optionally substituted as above, $(C_1-C_4)$alkoxy$(C_1-C_6)$alkyl, amino$(C_1-C_6)$alkyl, mono- or di-$(C_1-C_4)$alkylamino$(C_1-C_6)$alkyl, or a group $(CH_2)_m$—N—$(C_1-C_6)$alkyl ps wherein m is an integer selected from 3, 4, and 5, and one of the —$CH_2$— groups can be replaced by a heteroatom selected from O, S, and N;

$R_4$ represents hydrogen, $(C_1-C_4)$alkyl or benzyl; and the physiologically acceptable salts thereof.

DETAILED DESCRIPTION OF THE INVENTION $(C_1-C_6)$alkyl groups, as defined in the present application, include methyl, ethyl, propyl, isopropyl, n-butyl, isobutyl, pentyl, hexyl, and the like.

$(C_1-C_4)$alkyl groups and $(C_1-C_4)$alkoxy groups are groups of 1 to 4 carbon atoms, inclusive, which are included in the above definition of $(C_1-C_6)$alkyl groups and $(C_1-C_6)$alkoxy groups, respectively.

$(C_3-C_7)$cycloalkyl groups are cyclopropyl, cyclobutyl, cyclopentyl, cyclohexyl, and cycloheptyl groups.

$(C_1-C_6)$alkoxy groups include methoxy, ethoxy, propoxy, butoxy, pentoxy, and hexoxy groups.

The term "halo" represents halogen atoms selected from chloro, bromo, and fluoro, while halo$(C_1-C_4)$alkyl groups are halogenalkyl groups of 1 to 4 carbon atoms inclusive, wherein some or all the hydrogen atoms are replaced with halogen atoms. Representative examples of halo$(C_1-C_4)$alkyl groups are: trifluoromethyl, chlorodifluoromethyl, bromochlorofluoromethyl, trichloromethyl, 1,1-dichloroethyl, 1,2-dichloroethyl, 1-chloro-2,2,2-trifluorofluoroethyl, and the like.

"Physiologically acceptable salts" are pharmaceutically acceptable salts wherein the whole toxicity of the compound is not increased compared with the non-salt. These acid addition salts are obtained by treating compounds of the above formula I with pharmaceutically acceptable acids.

Representative examples of acids suitable for the formation of physiologically acceptable salts are: hydrohalide, sulfuric, phosphoric, and nitric acids; aliphatic, alicyclic, aromatic or heterocyclic carboxylic or sulfonic acids, such as formic, acetic, propionic, succinic, glycolic, lactic, malic, tartaric, citric, ascorbic, α-ketoglutaric, glutamic, aspartic, maleic, hydroxymaleic, pyruvic acid; phenylacetic, benzoic, para-aminobenzoic, anthranilic, para-hydroxybenzoic, salicylic, para-aminosalicylic or embonic acid, methanesulfonic, ethanesulfonic, hydroxyethanesulfonic, ethylenesulfonic acid; halobenzenesulfonic, toluenesulfonic, naphthalenesulfonic acids or sulfanilic acid.

These or other salts of the new compounds may also be used for purifying the resulting compounds by converting them into salts, isolating the latter and liberating the free compound from them. When according to the above outlined procedures, compounds of formula I are obtained as the corresponding salts of pharmaceutically acceptable acids, they may be converted into the corresponding free base by treatment with an alkali agent.

The free base may in turn be transformed into the corresponding salts by reaction with predetermined pharmaceutically acceptable acids. In view of the close relationship between the new compounds in the free form and in the form of their salts what has been said above and hereinafter with reference to the free compounds concerns also the corresponding salts.

A preferred group of compounds of the present invention are those of formula I wherein R and $R_1$ independently are hydrogen, ($C_1$-$C_6$)alkyl or phenyl, unsubstituted or substituted as above, $R_2$ is a phenyl group substituted by 1 or 2 substituents, selected from nitro, ($C_1$-$C_4$)alkoxy, ($C_1$-$C_4$)alkyl, chloro or trifluoromethyl, $R_3$ is ($C_1$-$C_6$)alkyl or ($C_1$-$C_4$)alkoxy($C_1$-$C_4$)alkyl, and $R_4$ is hydrogen, methyl or benzyl, or a corresponding physiologically acceptable acid addition salt.

Another preferred group of compounds are those compounds of formula I wherein R is hydrogen, methyl or phenyl, optionally substituted as above, $R_1$ is hydrogen, methyl, ethyl, isopropyl, sec-butyl, phenyl optionally substituted as above, $R_2$ is 2- or 3-nitrophenyl, 2- or 3-methylphenyl, or 2- or 3-trifluoromethylphenyl, $R_3$ is ($C_1$-$C_6$)alkyl, ($C_1$-$C_4$)alkoxy($C_1$-$C_6$)alkyl, and $R_4$ is hydrogen, or a corresponding physiologically acceptable acid addition salt.

More preferred compounds of this invention are those compounds of formula 1 wherein R is methyl, $R_1$ is isopropyl or sec-butyl, $R_2$ is 2-methylphenyl, $R_3$ is methyl, and $R_4$ is hydrogen. The most preferred compound of this invention is the compound of formula 1 wherein R is methyl, $R_1$ is sec-butyl, $R_2$ is 2-methylphenyl, $R_3$ is methyl, and $R_4$ is hydrogen, that is the compound methyl 4,7-dihydro-1,6-dimethyl-4-(2-methylphenyl)-3-(2-methylpropyl)-1H-pyrazolo[3,4-b]pyridine-5-carboxylate.

The compounds used in the present invention are known and can be prepared as described in, for example, European Patent Application Number 0114273, published Aug. 1, 1984.

The ability of the compounds of this invention to act as calcium channel blockers can be demonstrated by their ability to antagonize calcium-induced contractions in $K^+$-depolarized taenia of the Guinea pig caecum. Strips of taenia (1–2 mm diameter, 2–2.5 cm relaxed length), were dissected from the caecum of male guinea pigs (250–350 g) and set up in 20 ml isolated-organ baths containing $K^+$-depolarizing Tyrode solution maintained at 35° C. and gassed with 95% $O_2$ and 5% $CO_2$. The composition of the $K^+$-Tyrode solution was (mmol/l): NaCl 97; KCl 40; $NaHCO_3$ 11.9; $NaH_2PO_4$ 0.4; glucose 5.5; pH 7.1. Contractile responses were measured under isotonic conditions (1 g load) using a Harvard isotonic transducer connected to a Rikadenki potentiometric recorder.

Cumulative concentration response curves were obtained to $CaCl_2$ (30–3,000 μmol/l) by increasing the $Ca^{2+}$ concentration at 3 minute intervals in logarithmic increments, (Van Rossum, Arch. Int. Pharmacodyn., 143, 299–330, 1963)). A 20 minute washout period (6 changes of bathing fluid) was allowed between curves. The 100% response was taken as the maximum contractile response of the tissue during the second concentration response curve, and all subsequent contractions were calculated as a percentage of this value. Dose ratios were calculated as the ratio of the concentration of $Ca^{2+}$ which produced a 50% maximal response ($EC_{50}$) in the presence and absence of the antagonist. Apparent $pA_2$ values were calculated by the method of Arunlakshana and Schild, Br. J. Pharmac. Chemother., 14, 48–58, (1959), by plotting log (dose ratio-l) against negative log (molar concentration antagonist). Student's test was used for comparison of mean values. Values are expressed as mean ±SEM. All concentrations are the final concentration of drug in the bathing solution.

The compounds are initially tested at a fixed concentration (10 μg/ml). In these conditions the compounds of the invention show antagonism of $Ca^{2+}$ induced contractions in $K^+$-depolarized taenia. More particularly, the compounds:

methyl 4,7-dihydro-1,3,6-trimethyl-4-(2-nitrophenyl)-1H-pyrazolo[3,4-b]pyridin-5-carboxylate;

ethyl 4,7-dihydro-1,3,6-trimethyl-4-(2-nitrophenyl)-1H-pyrazolo[3,4-b]pyridin-5-carboxylate;

ethyl 4,7-dihydro-1,6-dimethyl-3-phenyl-4-(2-methylphenyl)-1H-pyrazolo[3,4-b]pyridin-5-carboxylate;

ethyl 4,7-dihydro-1,6-dimethyl-3-phenyl-4-(2-nitrophenyl)-1H-pyrazolo[3,4-b]pyridin-5-carboxylate;

methyl 4,7-dihydro-1,6-dimethyl-4-(2-nitrophenyl)-3-phenyl-1H-pyrazolo[3,4-b]pyridin-5-carboxylate;

ethyl 4,7-dihydro-1,6-dimethyl-3-(1-methylethyl)-4-(2-nitrophenyl)-1H-pyrazolo[3,4-b]pyridin-5-carboxylate;

methyl 4,7-dihydro-1,6-dimethyl-3-(1-methylethyl)-4-(2-nitrophenyl)-1H-pyrazolo[3,4-b]pyridin-5-carboxylate;

methyl 4,7-dihydro-1,6-dimethyl-3-(1-methylethyl)-4-(3-nitrophenyl)-1H-pyrazolo[3,4-b]pyridin-5-carboxylate;

methyl 4,7-dihydro-1,6-dimethyl-3-(2-methylpropyl)-4-(2-nitrophenyl)-1H-pyrazolo[3,4-b]pyridin-5-carboxylate;

methyl 4,7-dihydro-1,6-dimethyl-3-(2-methylpropyl)-4-(3-nitrophenyl)-1H-pyrazolo[3,4-b]pyridin-5-carboxylate; and 2-methoxyethyl 4,7-dihydro-1,6-dimethyl-3-(2-methylpropyl)-4-(2-nitrophenyl)-1H-pyrazolo3,4-b]pyridin-5-carboxylate show a $pA_2$ value in the range 8.2–9, cause concentration-dependent displacement to the right of cumulative concentration-response curves to $Ca^{2+}$, have a rapid onset of action, and cause a rapid relaxation of $Ca^{2+}$ (300 μM)-induced contractions at low concentrations (0.01–0.1 μM).

The anticonvulsive effect of the compound methyl 4,7-dihydro-1,6-dimethyl-4-(2-methylphenyl)-3-(2-methylpropyl)-1H-pyrazolo[3,4-b]pyridine-5-carboxylate (Methyl Ester) has been demonstrated in the following manner.

For controls, the convulsant $ED_{50}$ of pentylenetetrazol (PTZ) was determined 30' after vehicle administration by dosing groups of 10 or more mice with various iv doses of PTZ. For drug studies, groups of mice were given methyl ester or flunarizine, 8 or 16 mg/kg ip. Thirty minutes later, dose-response curves for PTZ were determined as described for controls. Convulsant $ED_{50}$ values (clonic and tonic) for PTZ for controls and each drug condition, as well as the significance of differences from control, were calculated with an appropriate computer program. Results are shown below.

| TREATMENT (mg/kg ip) | PTZ $ED_{50}$ mg/kg iv (95% C.L.) | |
|---|---|---|
| | clonic | tonic |
| Control | 26.9 (24.4–29.2) | 37.5 (34.8–40.7) |
| Methyl ester (8) | 38.4 (33.9–42.7)** | 47.1 (42.8–52.2)* |
| (16) | 42.5 (37.7–46.8)** | 48.9 (43.3–54.5)* |

| TREATMENT | PTZ ED$_{50}$ mg/kg iv (95% C.L.) | |
|---|---|---|
| (mg/kg ip) | clonic | tonic |
| Flunarizine (8) | ~34.6 (***) | 43.8 (40.2–47.8)* |
| (16) | 36.8 (31.4–41.9)* | 44.4 (38.7–49.7)* |

*p < .05 vs control
**dose-response functions not parallel to control
***no 95% C.L.; dose-response function too steep These data show the anticonvulsant activity for the methyl ester, a representative compound of this invention. Applicants believe the pyrazolopyridines of this invention will be of particular significance in the treatment of petit mal seizures.

Generally the compounds of the invention possess prolonged duration of action. In fact, representative examples possess a duration in animals of 8 to 12 hours or more at doses equal to the ED$_{50}$ value.

The compounds may be administered in various manners to achieve the desired effect. The compounds may be administered alone or in the form of pharmaceutical preparations to the patient being treated either orally or parenterally, such as, intravenously or intramuscularly. The formulation of suitable pharmaceutical compositions can be carried out by one skilled in the art according to the general common knowledge in the art, and referring to reference books, such as the "Remington's Pharmaceutical Sciences Handbook", Mack Publishing Company, U.S.A. The amount of compound administered will vary with the severity of the convulsant condition and the mode of administration. For oral administration the anticonvulsantly effective amount of compound is from about 0.01 mg/kg (milligrams per kilograms) of patient body weight per day to about 10 mg/kg of patient body weight per day and preferably from about 0.05 mg/kg of patient body weight per day to about 5 mg/kg of patient body weight per day.

For parenteral administration the anticonvulsantly effective amount of compound is from about 0.001 mg/kg of patient body weight per day up to about 5 mg/kg of patient body weight per day and preferably from about 0.01 mg/kg of patient body weight per day up to about 2 mg/kg of patient body weight per day.

For oral administration a unit dosage may contain, for example, from 0.50 to 100 mg of the active ingredient. For parenteral administration a unit dosage may contain, for example, from 0.05 to 70 mg of the active ingredient. Since the compounds of the invention generally possess a long lasting duration of action they might be conveniently administered once or twice a day, however, repetitive daily administrations may be, at least in some instances, desirable and will vary with the conditions of the patient and the mode of administration. As used herein, the term "patient" is taken to mean a warm blooded animal, humans included.

For oral administration the compounds can be formulated into solid or liquid preparations such as capsules, pills, tablets, troches, powders, solutions, suspensions or emulsions. The solid unit dosage form can be a capsule which can be of the ordinary gelatin type, either hard or soft, containing, for example, lubricants and inert fillers such as lactose, sucrose and cornstarch.

In another embodiment the compounds of the invention can be tabletted with conventional tablet bases such as lactose, sucrose and cornstarch in combination with binders such as acacia, cornstarch or gelatin, disintegrating agents such as potato starch or alginic acid, and a lubricant such as stearic acid or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of mineral petroleum, animal, vegetable or synthetic origin. For example, peanut oil, soybean oil and mineral oil. In general, water, saline, aqueous dextrose and related sugar solutions, ethanol and glycols such as propylene glycol or polyethylene glycol can be used as liquid carriers for injectable solutions.

For rectal administration the compounds are administered in the form of suppositories, admixed with conventional vehicles such as, for example, cocoa butter, wax, spermaceti, polyvinylpyrrolidone, or polyoxyethyleneglycols and their derivatives.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic ®, a silicone rubber manufactured by the Dow-Corning Corporation. The oral route is generally the peferred route of administration of the compounds of the invention, while the capsule is generally the preferred pharmaceutical formulation.

The following are illustrative pharmaceutical formulations which may be employed in practicing the present invention:

A capsule is prepared with:

| | |
|---|---|
| 2-Dihydro-1,6-dimethyl-4-(2-methylphenyl)-1H-pyrazolo[3,4-b]pyridin-5-carboxylic acid methyl ester | 50 mg |
| Saccharose | 10 mg |
| Polyvinylpyrrolidone | 2 mg |
| Sodium dioctylsulfosuccinate | 0.5 mg |
| Magnesium stearate | 2.5 mg |
| Corn starch | q.s. to 150 mg |

A tablet is prepared with:

| | |
|---|---|
| 4,7-Dihydro-1,6-dimethyl-4-(2-methylphenyl)-1H-pyrazolol[3,4-b]pyridin-5-carboxylic acid methyl ester | 50 mg |
| Polyvinylpyrrolidone | 2 mg |
| Sodium carboxymethylcellulose | 1.5 mg |
| Avicel ® | 5 mg |
| Titanium dioxide | 2 mg |
| Magnesium stearate | 2.5 mg |
| Cornstarch | 8 mg |
| Gum arabic | 5 mg |
| Talc | 10 mg |
| Kaolin | 2 mg |
| Saccharose | q.s. to 150 mg |

We claim:

1. A method for treating epilepsy in a patient in need thereof which comprises administering to the patient an anticonvulsantly effective amount of a compound of the formula

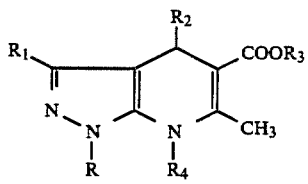

wherein
- R represents hydrogen, (C$_1$–C$_6$)alkyl, (C$_1$–C$_6$)alkenyl, (C$_3$–C$_7$) cycloalkyl, unsubstituted phenyl or a phenyl substituted by 1, 2 or 3 substituents selected from (C$_1$–C$_4$)alkyl, (C$_1$–C$_4$)alkoxy, chloro, fluoro, bromo, nitro, and (C$_1$–6) alkoxycarbonyl, unsubstituted phenyl (C$_1$–C$_4$)alkyl, or phenyl (C$_1$–C$_4$)alkyl substituted as above;
- R$_1$ represents hydrogen, (C$_1$–C$_6$) alkyl, (C$_2$–C$_6$)alkyl, (C$_2$–C$_6$)alkenyl, (C$_3$–C$_7$) cycloalkyl, (C$_1$–C$_6$)alkoxycarbonyl, unsubstituted phenyl or phenyl substituted as above, or unsubstituted phenyl(C$_1$–C$_4$)alkyl, or phenyl (C$_1$–C$_4$) alkyl substituted as above;
- R$_2$ represents unsubstituted phenyl groups or phenyl groups substituted with 1, 2 or 3 substituents selected from (C$_1$–C$_4$)alkyl, (C$_1$–C$_4$)alkoxy, halo(C$_1$–C$_4$)alkyl, chloro, bromo, fluoro, nitro, cyano, (C$_1$–C$_6$)alkoxycarbonyl, and a group of formula S(O)n-(C$_1$–C$_6$)alkyl, wherein n represents zero or the integer 1 or 2, or R$_2$ represents a pentafluorophenyl group, an α- or β-naphthyl group, an aromatic 5–6 membered heterocycle ring selected from the group consisting of furanyl or thienyl, a group of formula

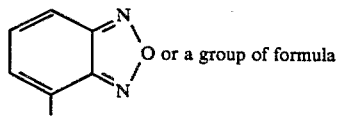 or a group of formula

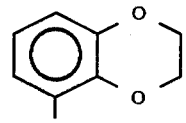

wherein
- R$_3$ represents (C$_1$–C$_6$)alkyl, (C$_2$–C$_6$)alkenyl, unsubstituted phenyl or phenyl substituted as above, and unsubstituted phenyl(C$_1$–C$_4$)alkyl or phenyl (C$_1$–C$_4$)alkyl substituted as above, (C$_1$–C$_4$)alkoxy-(C$_1$–C$_6$)alkyl, amino(C$_1$–C$_6$)alkyl, mono- or di-(C$_1$–C$_4$)alkylamino(C$_1$–C$_6$)alkyl,
- R$_4$ represents hydrogen, (C$_1$–C$_4$)alkyl or benzyl; or a physiologically acceptable salt thereof.

2. A method of claim 1 wherein R and R$_1$ independently are hydrogen, (C$_1$–C$_6$)alkyl or phenyl, unsubstituted or substituted as in claim 1; R$_2$ is a phenyl group substituted by 1 or 2 substituents, selected from nitro, (C$_1$–C$_4$)alkoxy, (C$_1$–C$_4$)alkyl, chloro or trifluoromethyl; R$_3$ is (C$_1$–C$_6$)alkyl or (C$_1$–C$_4$)alkoxy(C$_1$–C$_4$)alkyl; and R$_4$ is hydrogen, methyl or benzyl; or a corresponding physiologically acceptable acid addition salt thereof.

3. A method of claim 1 wherein R is hydrogen, methyl or unsubstituted phenyl or phenyl substituted as in claim 1; R$_1$ is hydrogen, methyl, ethyl, isopropyl, sec-butyl, or unsubstituted phenyl or phenyl substituted as in claim 1; R$_2$ is 2- or 3-nitrophenyl, 2- or 3-methylphenyl, or 2- or 3-trifluoromethylphenyl; R$_3$ is (C$_1$–C$_6$)alkyl, (C$_1$–C$_4$)alkoxy(C$_1$–C$_6$)alkyl, or R$_4$ is hydrogen, or a corresponding physiologically acceptable acid addition salt thereof.

4. A method of claim 3 wherein R is methyl; R$_1$ is isopropyl or sec-butyl; R$_2$ is 2-methylphenyl; R$_3$ is methyl; and R$_4$ is hydrogen; or a corresponding physiologically acceptable acid addition salt thereof.

5. A method of claim 4 wherein R is methyl; R$_1$ is sec-butyl; R$_2$ is 2-methylphenyl; R$_3$ is methyl; and R$_4$ is hydrogen; that is the compound methyl 4,7-dihydro-1,6-dimethyl-4-(2-methylphenyl)-3-(2-methylpropyl)-1H-pyrazolo[3,4-b]pyridine-5-carboxylate; or a corresponding physiologically acceptable acid addition salt thereof.

* * * * *

REEXAMINATION CERTIFICATE (1891st)

United States Patent [19]

Palfreyman et al.

[11] B1 4,916,140

[45] Certificate Issued Dec. 29, 1992

[54] ANTIEPILEPTIC PYRAZOLOPYRIDINES

[75] Inventors: Michael G. Palfreyman, Cincinnati; Francis P. Miller, Loveland, both of Ohio; Anis Mir, Bartenheim, France

[73] Assignee: Merrell Dow Pharmaceutical Inc., Cincinnati, Ohio

Reexamination Request:
No. 90/002,182, Oct. 29, 1990

Reexamination Certificate for:
Patent No.: 4,916,140
Issued: Apr. 10, 1990
Appl. No.: 250,478
Filed: Sep. 28, 1988

[51] Int. Cl.⁵ .............................. A61K 31/44
[52] U.S. Cl. .................................... 514/299
[58] Field of Search ..................... 514/299, 303

[56] References Cited

U.S. PATENT DOCUMENTS 4,562,256 12/1985 Adachi et al. .................. 546/120

FOREIGN PATENT DOCUMENTS 0114273 8/1984 European Pat. Off. .

OTHER PUBLICATIONS

Brodie, M. J., Br. Med. J., (296), pp. 530–531 (1988).
Binnie et al., Intl. Symposium on Calcium Antagonists, NYC (Feb. 1987).
Treiman, D. M., Intl. Symp. on $Ca^{2+}$ Antagonists, NYC (1987).
Meyer et al., Intl. Symp. on $Ca^{2+}$ Antagonists, NYC (1987).
Scriabine, Intl. Symp. on $Ca^{2+}$ Antag., NYC (1987).
Craig et al., *Modern Pharmacology*, (1st ed. 1982) pp. 416–418.

*Primary Examiner*—Frederick E. Waddell

[57] ABSTRACT

The disclosure pertains to certain pyrazolopyridincarboxylates which are calcium channel blockers and possess anticonvulsant properties. By virtue of this activity, the compounds are useful in the treatment of epilepsy.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-5 are cancelled.

* * * * *